United States Patent [19]

Rupp

[11] Patent Number: 5,718,694
[45] Date of Patent: Feb. 17, 1998

[54] INHIBITION OF ADHERENCE OF MICROORGANISMS TO BIOMATERIAL SURFACES BY TREATMENT WITH CARBOHYDRATES

[75] Inventor: Mark E. Rupp, Omaha, Nebr.

[73] Assignee: The Board of Regents of the University of Nebraska, Lincoln, Nebr.

[21] Appl. No.: 448,682

[22] Filed: May 24, 1995

Related U.S. Application Data

[63] Continuation-in-part of Ser. No. 149,607, Nov. 9, 1993, abandoned.

[51] Int. Cl.$^6$ .................................. A61M 25/00
[52] U.S. Cl. ................... 604/265; 609/890.1; 424/423; 424/461; 128/898
[58] Field of Search .................. 604/265, 266, 604/890.1, 891.1; 128/898; 424/422, 423, 461; 520/56, 58; 623/1, 11, 12

[56] References Cited

U.S. PATENT DOCUMENTS

| | | | |
|---|---|---|---|
| 4,668,224 | 5/1987 | Lentz et al. | 604/265 |
| 4,773,902 | 9/1988 | Lentz et al. | 604/265 |
| 4,906,237 | 3/1990 | Johansson et al. | 604/265 |
| 4,909,799 | 3/1990 | Thulesius et al. | 604/265 |
| 4,980,374 | 12/1990 | Steudle et al. | 514/557 |
| 5,055,455 | 10/1991 | Pier | 514/54 |
| 5,167,960 | 12/1992 | Ito et al. | 424/423 |
| 5,217,492 | 6/1993 | Guire et al. | 623/11 |
| 5,290,585 | 3/1994 | Elton | 427/2 |
| 5,295,978 | 3/1994 | Fan et al. | 604/265 |
| 5,360,415 | 11/1994 | Yabushita et al. | 604/265 |
| 5,366,505 | 11/1994 | Farber | 623/11 |
| 5,622,939 | 4/1997 | Jamas et al. | 514/54 |

FOREIGN PATENT DOCUMENTS

| | | | |
|---|---|---|---|
| 91/15252 | 10/1991 | WIPO | 604/266 |

OTHER PUBLICATIONS

Ruggieri et al., Journal of Urology, Aug. 1987, 138(2), pp. 423–426, "Inhibition of Bacterial Adherence to Catheter Latex Surfaces".

Vaudaux et al., Journal of Biomaterial, Science Polymer Addition, 1992, vol. 4, No. 2, pp. 89–97 (1992) "Inhibition by Heparin and Derivatized Dextrans of Staphylococcus Aureus Adhesion to Fibronectin–Coated Biomaterials".

Rupp, Hemagglutination and Adherence to Plastic by Staphylococcus Epidermidis (Infection and Immunity, Oct. 1992) vol. 60, No. 10, pp. 4322–4327.

Corona, Subspecialty Clinics: Critical–Care Medicine Infections Related to Central Venous Catheter (Mayo Clin. Proc 1990) 65:979–986.

Goldmann, Pathogenesis of Infections Related to Intravascular Catherization (Clinical Microbiology Rev 1993) pp. 176–192.

Gristina, Biomaterial–Centered Infection: Microbial Adhesion Versus Tissue Integration (Science Sep. 1987) vol. 237, pp. 1588–1595.

Hussain et al., JID Mar. 1991:163 "Isolation and Composition of the Extracellular Slime Made by Coagulase–Negative Staphylococci in a Chemically Defined Medium".

Christensen, et al., Infection and Immunity, Sep. 1990, vo. 58, No. 9:2906–2911 "Identification of an Antigenic Marker of Slime Production for Staphlococcus Epidermidis".

Drewry, et al., J. Clin. Microbi. Jun. 1990 vo. 28, No. 6:1292–1296 "Staphylococcal Slime: A Cautionary Tale".

*Primary Examiner*—Michael Powell Buiz
*Assistant Examiner*—Chalin Smith
*Attorney, Agent, or Firm*—Zarley, McKee, Thomte, Voorhees & Sease

[57] ABSTRACT

A method of inhibiting adherence of bacteria, fungus and other similar microorganisms to the surface of biomaterials is disclosed wherein biomaterials such as catheters and prosthetic devices are pretreated with a coating of a simple carbohydrate such as a mono- or di-saccharide. Intravascular catheters treated as such are shown to have significant reduction of adherence by *S. epidermidis*, *S. aureus*, Candidas and other organisms associated with nosocomial infection.

20 Claims, 5 Drawing Sheets

INHIBITION OF ADHERENCE OF MICROORGANISMS TO BIOMATERIAL SURFACES BY TREATMENT WITH CARBOHYDRATES

CROSS REFERENCE TO RELATED APPLICATION

This application is a Continuation-in-part application of U.S. application Ser. No. 08/149,607 by Mark E. Rupp filed Nov. 9, 1993 now abandoned. Both applications are commonly owned.

FIELD OF THE INVENTION

This invention is related to the field of antimicrobial treatments for prosthetic devices such as catheters, artificial joints and the like to prevent infection by microorganisms such as viruses, bacteria or fungi.

BACKGROUND OF THE INVENTION

Despite several advances in materials selected for catheters and other prosthetic devices, catheter infection and nosocomial bacteremia remain problematic for both physicians and patients. It is generally accepted that the pathogenesis of prosthetic device infection involves inoculation of small numbers of microorganisms, viruses, bacteria or fungi, such as *Staphylococcus epidermidis* (*S. epidermidis*), from the skin of the patient into the wound during implantation of the device. The microorganisms adhere to the biomaterial and then proliferate, resulting in a prosthetic device infection and in some cases bacteremia.

*S. epidermidis* bacteremia has an attributable mortality rate of 10–34%, results in an excess hospital stay of 8 days, and costs an estimated $6,000.00 per case. *S. epidermidis* is involved in these infections when the biomaterial surface consists of a polymer or when a polymer is a component of a complex device, such as extended wear contact lenses, vascular prostheses, intravascular catheters or total joints. Other bacteria such as *Staphylococcus aureus* tend to prefer adhesion to metals. Gristina, Anthony G. 1987. *Biomaterial-Centered Infection: Microbial Adhesion Versus Tissue Integration*, SCIENCE, 237:1588–1595. As used herein the term biomaterial refers to non-metallic surfaces for which bacteria have a tendency to adhere when used in contact with body parts. Examples include: substantially inert polymeric materials such as polymeric alpha olefins such as polyethylene, Teflon, or other plastics used in formation of intravascular catheters, vascular prostheses, prosthetic heart valves, artificial joints, and the like.

*S. epidermidis* is a generally avirulent commensal organism of the human skin, and is the principle etiologic agent of infections of peripheral and central venous catheters, prosthetic heart valves, artificial joints, and other prosthetic devices. Despite its importance as a nosocomial pathogen, relatively little is known about the pathogenesis of these infections or the virulence determinants of this organism. Vascular catheters are thought to become infected when microorganisms gain access to the device, and hence the blood stream, by migration from the skin surface down the transcutaneous portion of the catheter. In short term catheters this occurs primarily along the external surface of the catheter. In long term devices, colonization of the catheter hub and migration via the internal lumen may be important.

In either case, after inoculation, the organisms adhere to the prosthetic device or catheter and proliferate in association with the foreign body. Thus the skin serves as a large unlimited reservoir for *S. epidermidis*, and other bacterial, viral or fungal organisms.

Despite several advances in materials used for these prosthetic devices, from the early devices made of stainless steel or metallic materials to current less reactive plastics and polymers; bacteremia and nosocomial infections still remain. Currently intravascular catheters in common usage are constructed of polyurethane or some other plastic or siliconized rubber, and they are often coated with Teflon. These catheters are soft, flexible, nonreactive, and generally well tolerated.

Other attempts to decrease the incidence of infection associated with catheters and prosthetic devices have concentrated on techniques for implantation or special treatments for the device.

The first of these developments was the incorporation of a tissue barrier between the blood stream and the external environment. This was achieved by tunneling the catheter underneath the subcutaneous tissues (Hickman or Broviac catheters), or totally implanting the catheters in the subcutaneous space (Port-A-Cath or Infuse-A-Port catheters).

Other attempts included construction of catheters with antimicrobial properties. Catheters have been coated with various antibiotics and antiseptics such as Dicloxacillin, Cefazolin, Clindamycin, Fusidic Acid, and Chlorhexidine. Still further improvements include silver impregnated subcutaneous cuffs which have been attached to catheters in order to prevent migration of microorganisms via the external surface of the catheter. While these techniques may have provided limited success at controlling the spread of infection, a more efficient method would concentrate on the initial stage of pathogenesis, adherence.

Bacterial or microorganism adherence is thought to be the first crucial step in the pathogenesis of a prosthetic device infection. A number of factors influence an organism's ability to adhere to prosthetic material. These include characteristics of the microorganism (fungal, bacterial or viral) and the biomaterial, and the nature of the ambient milieu. The early stages of adherence are influenced by nonspecific forces such as surface charge, polarity, Van der Waals forces and hydrophobic interactions. Later stages of adherence are thought to involve more specific interactions between adhesins and receptors.

To date, investigation concerning the adherence of *S. epidermidis* to biomaterials has concerned itself primarily with the role of the extracellular polysaccharide or glycocalyx, also known as slime. Despite intensive study however, the proposed role of slime in the pathogenesis of disease or even its composition remain debated. Drewry, D. T., L. Gailbraith, B. J. Wilkinson, and S. G. Wilkinson. 1990. *Staphylococcal Slime: a Cautionary Tale*. J. Clin. Microbiol. 28:1292–1296. Currently, extracellular slime is thought to play a role in the later stages of adherence and persistence of infection. It may serve as an ion exchange resin to optimize a local nutritional environment, prevent penetration of antibiotics into the macrocolony, and protect bacteria from phagocytic host defense cells.

Peters et al have shown by electronmicroscopy studies that extracellular polysaccharide appears in the later stages of attachment and is not present during the initial phase of adherence. Peters, G., R. Locci, and G. Pulverer, 1982. *Adherence and Growth of Coagulase-Negative Staphylococci on Surfaces in Intravenous Catheters*. J. Infect. Dis. 146:479–482. Hogt et al demonstrated that removal of the extracellular slime layer by repeated washing does not diminish the ability of *S. epidermidis* to adhere to biomaterials. Hogt, A. H., J. Dankert, J. A. DeVries, and J. Feijen, 1983. *Adhesion of Coagulase-Negative Staphylococci to Biomaterials. J. Gen. Microbiol.* 129:2959–2968.

Thus study of exopolysaccharide has lended little to prevention of initial adherence by the bacteria.

Several other studies have identified other potential adhesins of *S. epidermidis* including the polysaccharide adhesion (PS/A) observed by Tojo et al. Tojo, M., N. Yamashita, D. A. Goldmann, and G. B. Pier, 1988. *Isolation and Characterization of a Capsular Polysaccharide Adhesin from Staphylococcus epidermidis.* J. Infect. Dis. 157:713–722. The slime associated antigen at (SAA) of Christensen et al. Christensen, G. D., Barker, L. P., Manhinnes, T. P., Baddour, L. M., Simpson, W. A. *Identification of an Antigenic Marker of Slime Production for Staphylococcus epidermidis.* Infect Immun. 1990; 58:2906–11.

It has been demonstrated that PS/A is a complex mixture of monosaccharides and purified PS/A blocks adherence of PS/A producing strains of *S. epidermidis.* In an animal model of endocarditis antibody directed against PS/A was protective. However it is not clear whether this protective effect was specific, related to anti-adhesive effects of the antibody, or due to a more generalized increase in the efficiency of opsonophagocytosis of blood borne bacteria. More recently isogenic mutants produced by Tn917 transposon mutagenesis were characterized. It appears that PS/A, SAA, and the polysaccharide antigen of Mack et al are distinct.

It has been hypothesized that each functions in different stages of the adherence process with one or more of these adhesins responsible for initial attraction while other are needed for aggregation in the macro colonies.

Despite all of this study, factors involved in the initial adherence of *S. epidermidis* and other infectious microorganisms to biomaterials remain largely unknown and equally unknown is a practical method for preventing the first stage of infection, adherence. It is an objective of the present invention to provide a pretreatment procedure for prosthetic devices which will reduce initial adherence of pathogenic microorganisms.

It is yet another object of the invention to reduce the incidence of nosocomial bacteremia and prosthetic device infection by preventing bacterial adherence to prosthetic devices.

Yet another object is to provide a method information on microorganism adherence to prosthetics and the role of carbohydrates in adherence.

Other objects of the invention will become obvious from the detailed description of the invention which follows.

SUMMARY OF THE INVENTION

This invention relates to a method of inhibiting adherence of microorganisms to prosthetic-devices by pretreating the surface of these devices with simple carbohydrates such as mono- or di-saccharides. In accordance with the present invention, a catheter or other such prosthetic device is coated with a mono-or disaccharide or a solution containing said saccharide or is incubated overnight in media containing mono or disaccharide.

Bacterial strains previously shown to mediate hemagglutination, an indicator of adherence, when exposed to devices so treated exhibit marked reduction in their ability to adhere to the devices. Quite surprisingly the procedure was found to reduce adherence of other bacterial strains as well including *Enter. feacium, E. Coli, S. aureus* and even fungal organisms such as Candidas. Thus by preventing microorganism adherence, bacteremia and other related infections will be reduced.

DETAILED DESCRIPTION OF THE INVENTION

This invention relates to the discovery that a pretreatment of catheters and/or prosthetic devices consisting essentially of a coating of mono-or disaccharides such as β-lactose, glucose and galactose greatly inhibits adherence of bacteria and fungi to the device.

Hemagglutination is the aggregation of erythrocytes caused by bacteria adhering to one or more erythrocytes. Hemagglutination is a commonly used assay to demonstrate bacterial adherence and, in gram negative organisms, has been shown to reflect specific lectin-receptor interactions that are important in the pathogenesis of disease. Hemagglutination by gram negative organisms has been intensively studied as a model of adherence. The hemagglutins are often proteins located on filamentous organelles that interact specifically with carbohydrate receptors on the surfaces of erythrocytes and other eukaryotic cells. These lectin-receptor interactions are important for the adherence of bacteria to mucosal surfaces, which is recognized as a vital first step in the pathogenesis of many diseases.

It has previously been shown that hemagglutination is strongly associated with adherence to polymers by the bacteria *S. epidermidis* and thus may play a major role in prosthetic device infection and serves as an easily demonstrable marker for adherence prone isolates. See Rupp, Mark E. and Archer, Gordon L. 1992. *Hemagglutination and*

Figure 1:
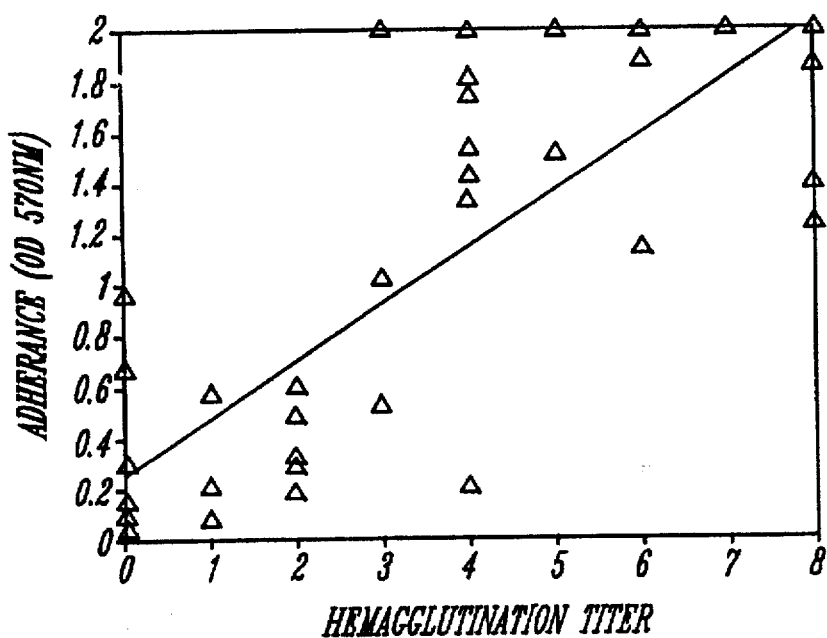
FIG. 1 is a linear regression plot of hemagglutination versus adherence for intravascular catheter associated strains of *S. epidermidis*.
Figure 2:
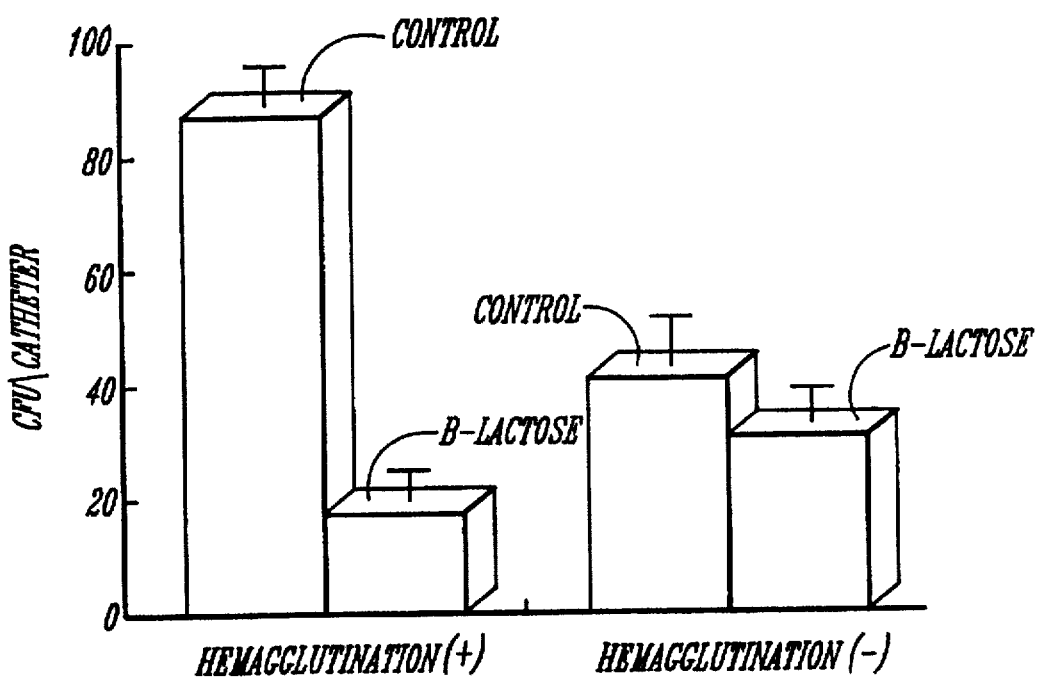
FIG. 2 is a graph demonstrating inhibition of adherence of *S. epidermidis* to Teflon catheters by treatment of bacteria with 0.5 molar β-lactose using the roll plate assay and incubation technique.
Figure 3:
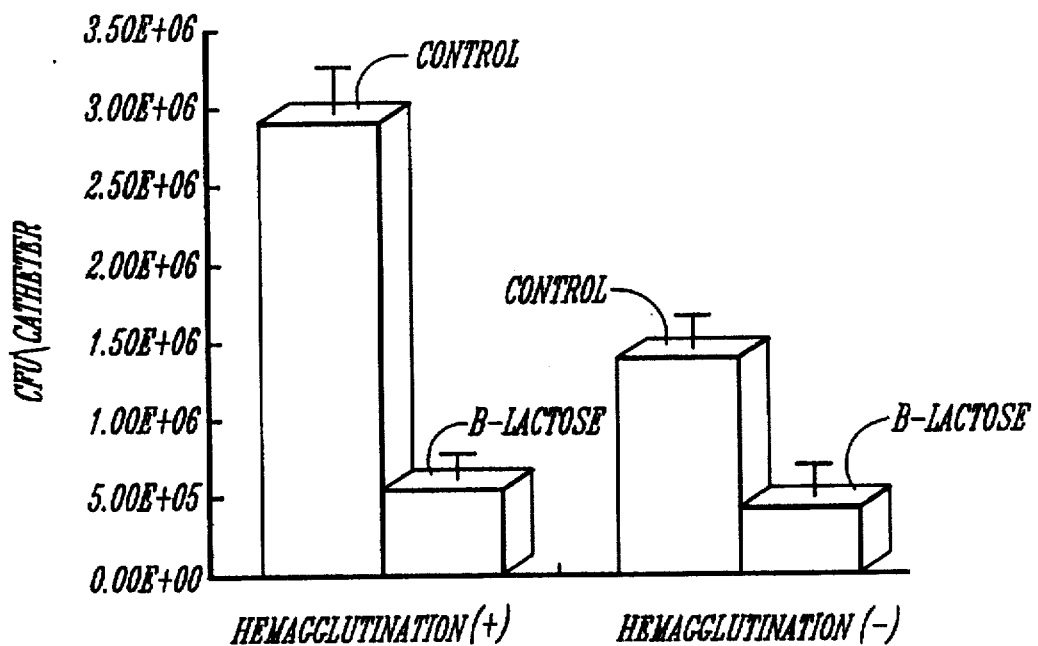
FIG. 3 is a graph demonstrating inhibition of adherence of radiolabeled bacteria by treatment with β-lactose using the incubation treatment method.
Figure 4:
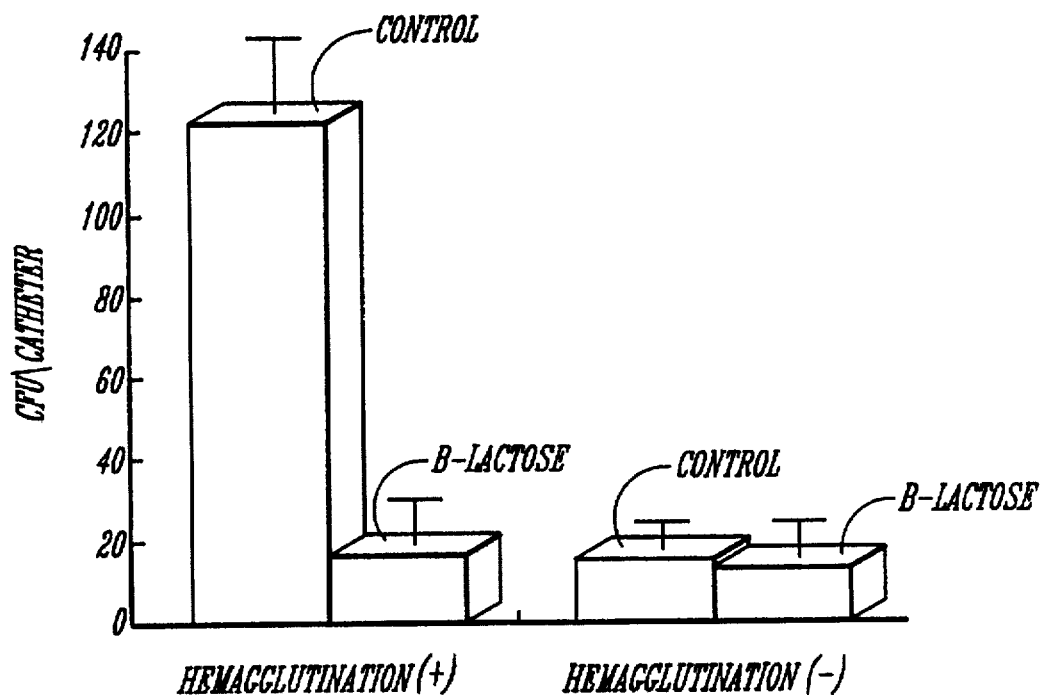
FIG. 4 is a graph depicting inhibition of bacterial adherence by treatment with β-lactose using catheter treatment method.

*Adherence to Plastic by S. epidermidis*, Infection and Immunity, 4322–4327, incorporated herein by reference. FIG. 1 is a graph demonstrating the significant association between hemagglutination of erythrocytes and adherence of *S. epidermidis* to biomaterials as measured by a quantitative spectrophotometric assay. Linear regression equation: (adherence)=(0.277) (hemagglutination titer)+(0.22): p<0.001 and R=0.87. This association has been shown to be significant when the number of types of erythrocytes or the titer of hemagglutination is examined. Further epidemiologic studies have indicated that hemagglutination is significantly more common among isolates responsible for Prosthetic Valve Endocarditis (PVE) compared to preoperative skin isolates from cardiac surgery patients. Thus hemagglutination provides a good indicator of bacterial adherence for *S. epidermidis* and a model for study of strains which will exhibit high degrees of adherence to prosthetic devices.

In accordance with the present invention a series of microorganisms were screened with pretreatment of mono- and di-saccharides and subsequent adherence of the organisms to biomaterials was observed. The mono and disaccharides were selected for study on the basis of their demonstrated capability of serving as receptors for other bacterial hemagglutins and lectins, and included: galactose, fructose, xylose, glucose, β-lactose, mannose, N-acetyl-D-Glucosamine, N-acetyl-D-Galactosamine N-acetylneuramic acid, and ribose. All of these exhibited significant inhibitory effects on hemagglutination of *S. epidermidis* and these were tested for corresponding inhibitory effects on adherence to the surfaces of biomaterials. Adherence was measured for both hemagglutination positive (HA+) and hemagglutination negative (HA−) strains of *S. epidermidis* by using a roll-plate semi-quantitative culture technique as introduced by Maki et al, or by using radiolabelling as a quantitative technique. Further, though less pronounced, the inhibition was also experienced by hemagglutination-negative strains indicating that other mono and disaccharides not initially studied may also prove useful see., Rupp et al supra. In fact the monosaccharide β-lactose was shown to work in reducing adherence of not only *S. epidermidis* but also of *S. aureus, Enter. feacium,* Pseodomonas, Klebsilla, *E. Coli, bacillus* and even the fungus Candidas.

While not wishing to be bound by any theory it is proposed that the hemagglutinin or other adhesin of *S. epidermidis* exerts its influence on adherence of the organism to polymer containing biomaterials by interacting with the device or with a conditioning film consisting of host glycoproteins which coats these devices after implantation. It has been shown that *S. epidermidis* adheres to polymers at a higher rate than *Staphylococcus aureus* does. Examination of several strains of *S. aureus* disclosed no similar hemagglutination. This may in part explain the differences in adherence between these two closely related species of Staphylococci that are observed. In addition, numerous studies have shown that human plasma proteins enhance the adherence of *S. aureus* to medical polymers. This relationship is less clear with coagulase-negative Staphylococci. Fimbriae and other proteinaceous adhesions may play a crucial role in the adherence process by reacting specifically with host receptors found in this conditioning film, or they may exert their influence by hydrophobic, electrostatic, or other nonspecific interactions. It is via this mechanism that we have hypothesized the hemagglutinin of *S. epidermidis* to exert its influence in the adherence of this organism to polymer containing biomaterials.

In accordance with the present invention, polymer containing biomaterials such as catheters or other prosthetic devices are treated with mono or disaccharides in a solution from 0.01M to 0.5M. Adherence of hemagglutination-positive strains *S. epidermidis* has been shown to decrease when the bacteria are incubated overnight in the presence of these carbohydrates, when a catheter is coated with the carbohydrate by incubating the catheter in a 0.5M carbohydrate solution or by including the carbohydrate in a 15 minute catheter/bacteria incubation period. To a lesser extent, adherence of hemagglutination-negative strains of *S. epidermidis* has also been shown to decrease in response to treatment with carbohydrates, other bacterial and fungal organisms have also exhibited reduced adherence with the saccharide pretreatment.

EXAMPLE 1

27 strains of *S. epidermidis* which had previously been tested for hemagglutination, See, Rupp et al, supra were used to test their ability to adhere to carbohydrate treated catheters, 18 were hemagglutination-positive and 9 were hemagglutination-negative. The affect was much greater for hemagglutination positive (thus highly adhering strains) as opposed to hemagglutination negative strains, however both experienced inhibition of adherence. Two methods were used to measure adherence of bacteria to intravascular catheters. The first was a variation on the role-plate method introduced by Maki et al, New England Journal of Medicine 296:1305–09 1977, which is incorporated herein by reference.

Briefly, bacteria were incubated overnight in Trypticase Soy Broth (TSB) at 37° C., harvested by centrifugation, washed, and resuspended in Phosphate Buffered Saline (PBS). The inoculum was standardized by McFarland turbidity standards and bacteria plate counts to $10^5$ CFU/ml. Next, 1 inch segments of Teflon intravascular catheter (Quik-Cath$^R$, Baxter) were immersed in the bacterial suspension for 15 minutes at room temperature. The catheter segments were then washed vigorously in PBS on an automated shaker (48 oscillations/min, +45° to −45°) for 10 minutes, changing the wash solution after 5 min, 3 min, and 2 min. It should be noted that a fifteen minute incubation period was used for the assay because it was designed to measure factors important in the early stages of adherence. The adherent bacteria were then quantitated by rolling the catheter on agar plates, which were incubated overnight at 37° C. and finally by counting the colonies of bacteria that develop after incubation.

Secondly, because there was potential for technician dependent error in the roll-plate method (for example variation in how hard they pressed down on the agar plates when they roll the catheter), radiolabeled bacteria were also used to quantify the colonies. For this method bacteria were radiolabeled by incubation in TSB containing 10μ Ci/ml of [methyl-$H^3$]-Thymidine (Amersham Corp) overnight at 37° C. Bacteria were harvested by centrifugation, washed, and resuspended in PBS. Inoculum was quantitated by scintillation count and bacterial plate count. Catheter segments were incubated in the bacterial suspension and washed as discussed above. CFU/cath was calculated from CPM. Inoculum size was normalized to $5 \times 10^8$ CFU/ml.

Using either quantitative method there was shown a significant decrease in adherence of *S. epidermidis* in the presence of β-lactose, fructose, galactose or glucose. This was demonstrated by two different experimental techniques which had reproducible results. The first, termed catheter pretreatment, in which the catheters were coated with the sugar by incubating them in 0.5M sugar solution overnight at room temperature. Another technique included incubation treatment, where the sugar (final concentration 0.5M) was included in the 15 minute bacteria/catheter incubation period.

All tests were performed in triplicate. The adherence data was analyzed for significance using the Wilcoxon signed rank test. Statistical evaluations were performed with Systat software.

Each of the sugars, glucose, galactose, fructose and β-lactose demonstrated inhibitory effects on bacterial adherence, especially for hemagglutination-positive strains.

In addition, electron microscopy studies were performed. Bacterial adherence assays were carried out as discussed above. The catheters were then fixed in 2% glutaraldehyde in 0.1M phosphate buffer for 1 hour. The catheters were dehydrated in an ascending concentration series of ethanol baths ending with Freon 113. Catheters were air-dried in a vacuum oven at 22° C., mounted on aluminum stubs, sputter coated with gold, and examined with a Philips 515 scanning electron microscope. Although the electron microscopy studies were conducted in an unblinded fashion, a marked inhibition of adherence was evident with β-lactose treatment.

Figure 8:
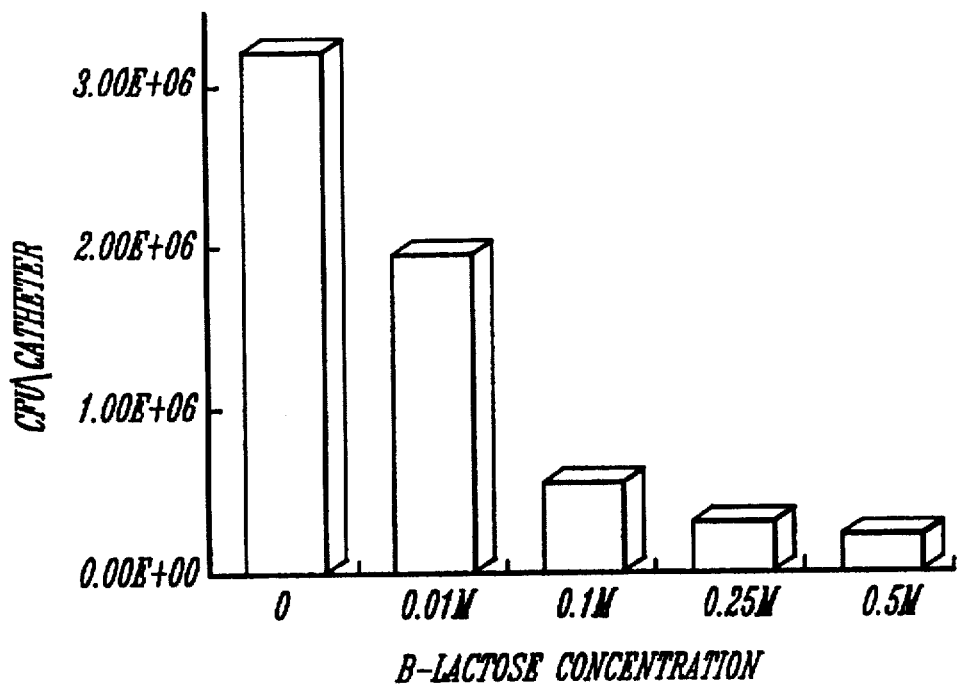
FIG. 8 is a graph depicting the concentration dependent inhibition of adherence with β-lactose using the incubation treatment and radiolabeled assay.

As can be seen in tables 1–4 and FIGS. 2–5, β-lactose exhibited a significant reduction in inhibition of adherence (up to greater than 90% for treated versus untreated catheters in hemagglutination positive strains). This was shown by the incubation method FIG. 2; (which results were reproduced by radiolabelled bacteria quantitation, FIG. 3), and the catheter treatment method, FIG. 4.) Also with β-lactose, it was demonstrated that there is a strong dose-response effect see FIGS. 8 and 9. At low concentrations of β-lactose there was a correspondingly low level of adherence inhibition.

TABLE 1

CARBOHYDRATE INHIBITION OF ADHERENCE

| Incubation Treatment | Roll-Plate Method Mean Adherence CFU/Catheter | |
|---|---|---|
| β-Lactose | Control | β-Lactose |
| HA(+) | 87 | 17 |
| HA(−) | 42 | 30 |
| HA(+) P = 0.000196 | | |
| HA(−) P = 0.035 | | |

NOTE: for all experiments
HA(+) = hemagglutination-positive,
HA(−) = hemagglutination-negative
18 strains of HA(+)
9 strains of HA(−)

TABLE 2

| Incubation Treatment | Radiolabeled Mean Adherence | |
|---|---|---|
| β-Lactose | Control | β-Lactose |
| HA(+) | 2.8 × 10⁶ | 5.3 × 10⁵ |
| HA(−) | 1.36 × 10⁶ | 4 × 10⁵ |

HA(−) P = 0.008
HA(+) P < 0.001

TABLE 3

CARBOHYDRATE INHIBITION OF ADHERENCE

| Catheter Treatment | Roll-Plate Method Mean Adherence CFU/Catheter | |
|---|---|---|
| β-lactose | Control | β-lactose |
| HA(+) | 124 | 15 |
| HA(−) | 14 | 13 |

HA(+) P = 0.000196
HA(−) P = 0.0138

Figure 5:
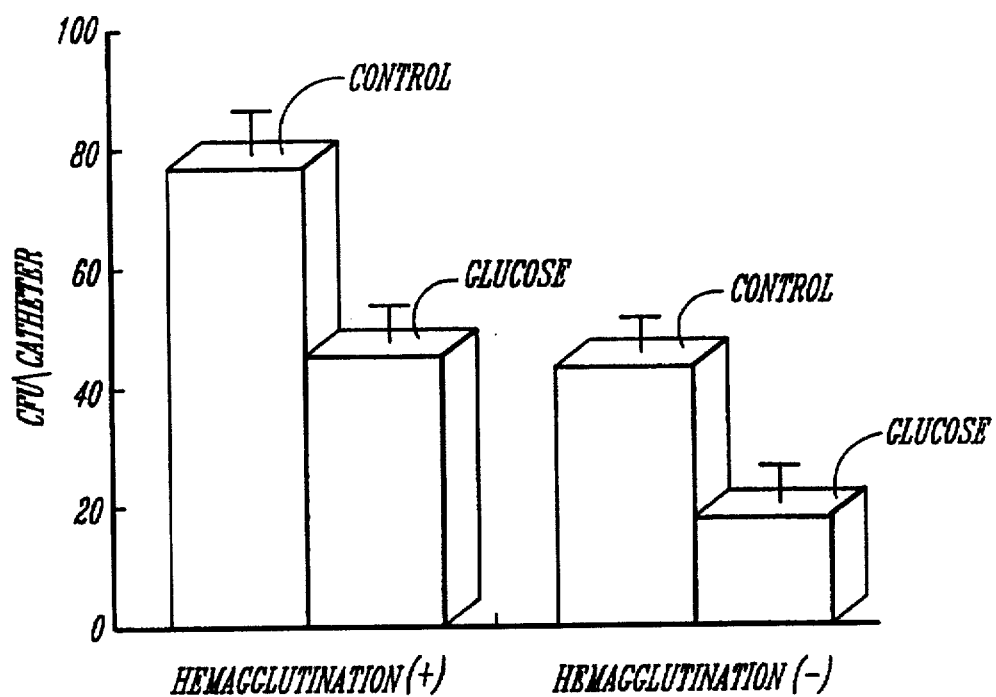
FIG. 5 is a graph demonstrating inhibition of adherence by treatment with glucose as shown by the roll-plate method using incubation treatment.
Figure 6:
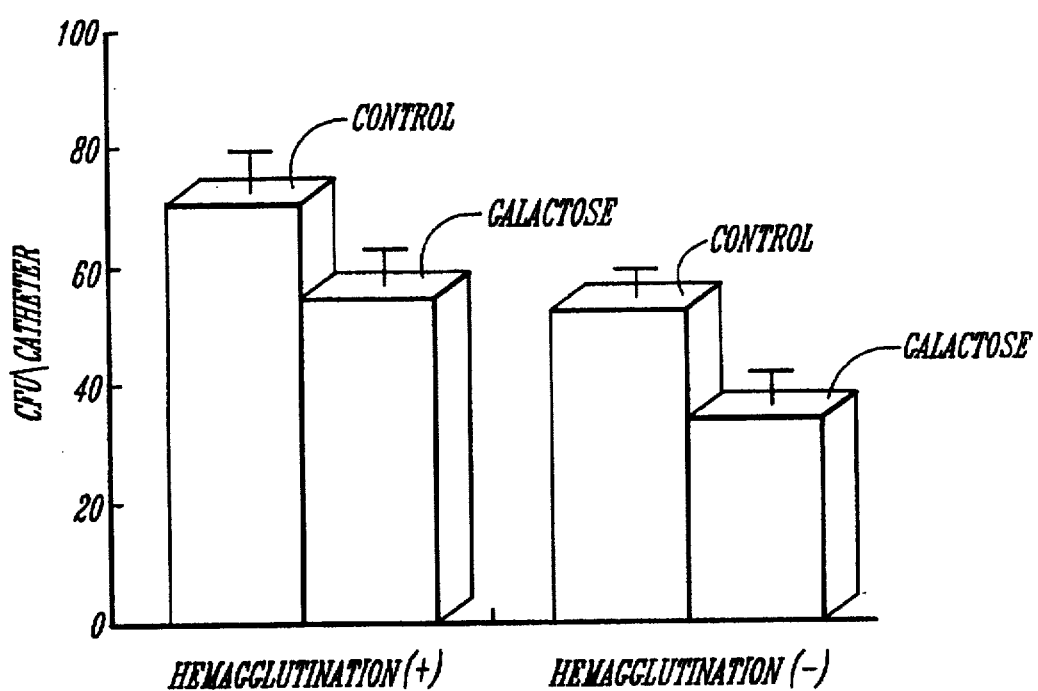
FIG. 6 is a graph demonstrating inhibition of adherence by treatment with galactose using the roll-plate method and incubation treatment.
Figure 7:
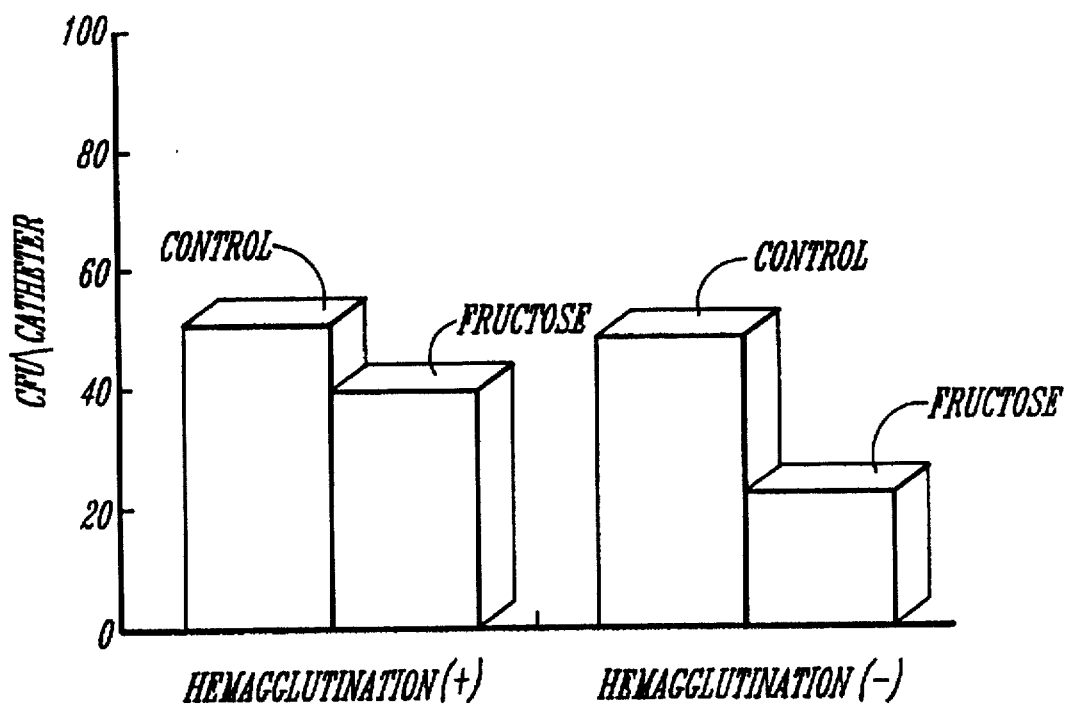
FIG. 7 is a graph demonstrating inhibition of adherence by treatment with fructose using the roll-plate method and the incubation technique.

The same experimental procedure as described was repeated using glucose, FIG. 5 and table 4, galactose FIG. 6 and table 5, and fructose, FIG. 7 and table 6.

TABLE 4

CARBOHYDRATE INHIBITION OF ADHERENCE

| Incubation Treatment | Roll-Plate Method Mean Adherence CFU/Catheter | |
|---|---|---|
| Glucose | Control | Glucose |
| HA(+) | 77 | 44 |
| HA(−) | 45 | 18 |
| HA(+) P = 0.002 | | |
| HA(−) P = 0.008 | | |

TABLE 5

CARBOHYDRATE INHIBITION OF ADHERENCE

| Incubation Treatment | Roll-Plate Method Mean Adherence CFU/Catheter | |
|---|---|---|
| Galactose | Control | Galactose |
| HA(+) | 71 | 55 |
| HA(−) | 53 | 34 |
| HA(+) P = 0.02 | | |
| HA(−) P = 0.068 | | |

TABLE 6

CARBOHYDRATE INHIBITION OF ADHERENCE

| Incubation Treatment | Roll-Plate Method Mean Adherence CFU/Catheter | |
|---|---|---|
| Fructose | Control | Fructose |
| HA(+) | 52 | 40 |
| HA(−) | 50.2 | 23 |
| HA(+) P = 0.067 | | |
| HA(−) P = 0.028 | | |

All demonstrated significantly less bacterial adherence in the presence of carbohydrates. It should also be noted that the reduction in adherence was observed in hemagglutination-negative bacterial strains as well as hemagglutination-positive strains. The most significant effect, however, was seen for the hemagglutination-positive strains.

From the foregoing it can be seen that the invention accomplishes at least all of its objectives.

EXAMPLE 2

Other Organisms

Figures 9, 10:
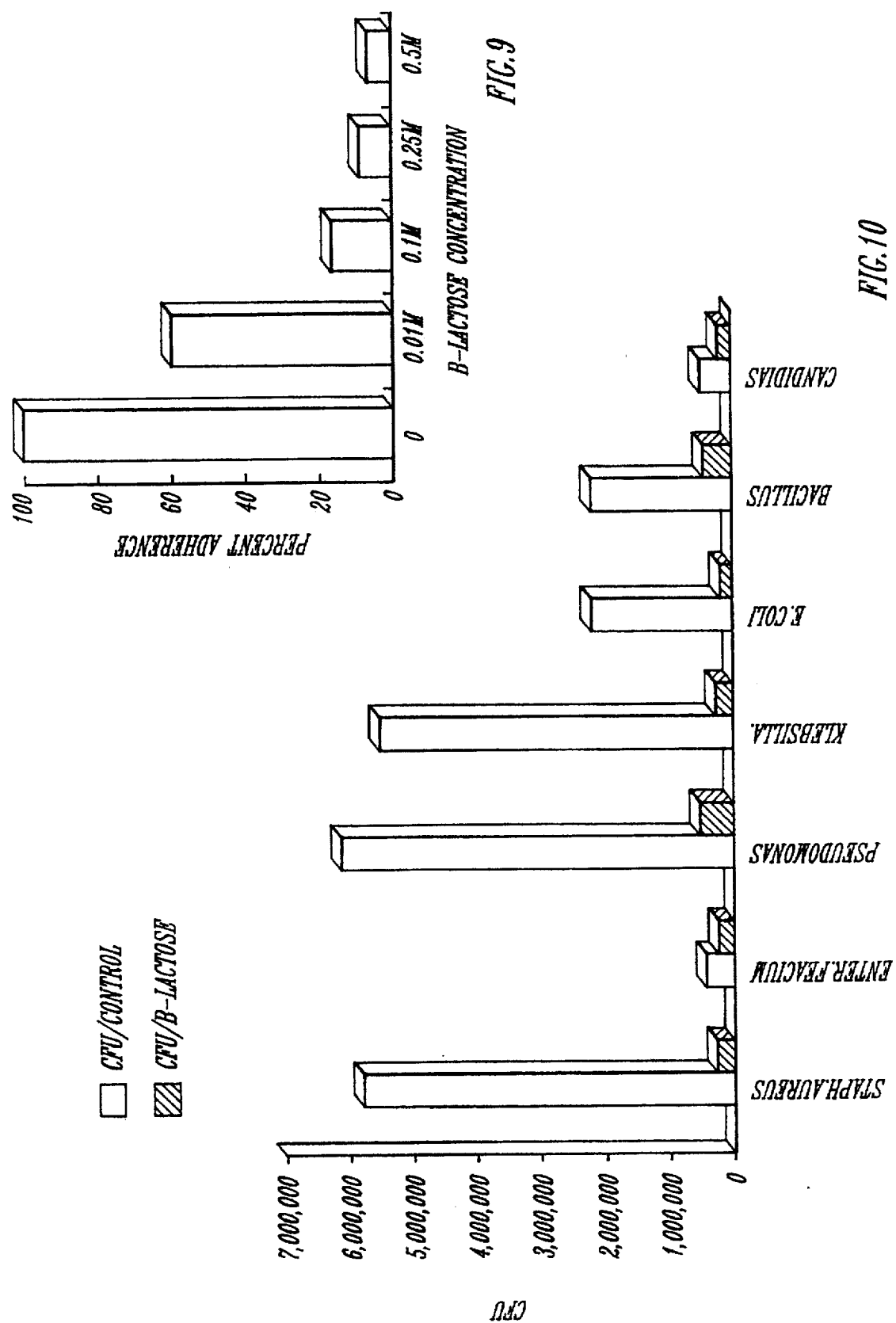
FIG. 9 is a graph depicting percent adherence vs. β-lactose concentration using incubation treatment and radiolabeled assay of FIG. 8.
FIG. 10 is a graph depicting the reduction in adherence of several bacterial and even a fungal microorganism with treatment with bacterial adherence.

FIG. 10 depicts the results of further studies exhibiting decreased adherence of a variety of other organisms. Briefly, catheters were coated with β-lactose as previously described and adherence was assayed by the roll-plate method. Adherence of a variety of bacterial and fungal organisms was drastically reduced anywhere from 60–96% when the method of the invention was employed. Table 7 below depicts the results.

TABLE 7

| Organism | % of decrease | CFU/ml | CPM/ml | CPM/CFU | CFU/control | CFU/β-Lactose |
|---|---|---|---|---|---|---|
| Staph. aureus | 96 | 1.05E+09 | 384500 | 3.60E–04 | 5.80E+06 | 2.10E+05 |
| Enter. feacium | 60 | 1.80E+08 | 1038230 | 5.0E–03 | 4.30E+05 | 1.70E+05 |
| Pseudomonas | 92 | 9.40E+08 | 89030 | 9.40E–05 | 6.10E+06 | 4.40E+05 |
| Klebsilla. | 96 | 1.03E+09 | 299360 | 2.90E–04 | 5.50E+06 | 2.40E+05 |
| E. coli | 96 | 6.10E+08 | 328780 | 5.30E–04 | 2.10E+06 | 9.80E+04 |
| Bacillus | 82 | 3.40E+08 | 316700 | 9.30E–04 | 2.10E+06 | 3.60E+05 |
| Candidias | 65 | 7.00E+07 | 141650 | 2.00E–03 | 4.00E+05 | 1.40E+05 |

What is claimed is:

1. A method of reducing adherence of microorganisms to polymer containing biomaterials comprising:

treating said biomaterial with a coating consisting essentially of a non-bacterially derived mono- or di-saccharide.

2. The method of claim 1 wherein said mono- or di-saccharide coating is a solution of from about 0.01M to 0.5M.

3. The method of claim 1 wherein said treatment includes coating said biomaterial with a solution of mono or disaccharide.

4. The method of claim 1 wherein said mono or disaccharide is selected from the group consisting of β-lactose, glucose, galactose, mannose, fructose, N-acetyl-D-glucosamine, N-acetyl-D-galactosamine, N-acetyl-neuraminic acid, ribose or xylose.

5. The method of claim 4 wherein said biomaterial is a catheter.

6. The method of claim 5 wherein said catheter is Teflon-coated.

7. The method of claim 1 wherein said biomaterial is a prosthetic device.

8. The method of claim 1 wherein said microorganism is a bacteria or a fungus.

9. The method of claim 7 wherein said bacteria or fungus is selected from the group consisting of: S. aureus, Enter. feacium, Pseudomonas, Klibsilla, E. coli, bacillus, Candidas.

10. A method of inhibiting microorganism adherence and concomitant biomaterial related infection comprising:

coating said biomaterial with a solution consisting essentially of a non-bacterially derived mono- or di- saccharide.

11. The method of claim 10 wherein said bacteria is S. epidermidis.

12. The method of 10 wherein said bacteria is hemagglutination positive.

13. The method of 10 wherein said bacteria is hemagglutination negative.

14. The method of claim 10 wherein said biomaterial contains a polymer.

15. The method of claim 10 wherein said biomaterial is plastic.

16. The method of claim 10 wherein said mono- or di-saccharide is selected from the group consisting of β-lactose, galactose, glucose and fructose.

17. A method of reducing microorganism adherence to biomaterial surfaces comprising:

treating said biomaterial surfaces with a coating of mono- or di-saccharide, said mono- or di-saccharide being non-bacterially derived and capable of serving as a receptor for bacterial hemagglutins and lectins.

18. A method of reducing adherence of microorganisms to polymer containing biomaterials comprising:

treating said biomaterial with a coating consisting essentially of β-lactose.

19. A method of reducing adherence of microorganisms to polymer containing biomaterials comprising:

treating said biomaterials with a coating comprised of mono- or di-saccharide to form a treated biomaterial;

wherein said treated biomaterials are effective in reducing adherence of methicillin-sensitive and methicillin-resistant Staphylococcus aureus, Enterococcus species, Staphylococcus epidermidis, gram-negative bacilli including E. coli, Enterobacter cloacae, Klebsiella pneumoniae, Pseudomonas aeruginosa, and Candida albicas.

20. A method of reducing adherence of microorganisms, said microorganisms comprising those whose adherence is not inhibited by a substantially pure bacterial polysaccharide adhesin, said method comprising:

treating said biomaterials with a coating comprised of mono- or di-saccharide.

* * * * *